(12) United States Patent
Frost (10) Patent No.: US 8,236,036 B1
(45) Date of Patent: Aug. 7, 2012

(54) OPTICAL DERMATOLOGICAL AND MEDICAL TREATMENT APPARATUS HAVING REPLACEABLE LASER DIODES

(76) Inventor: Ricky A. Frost, Tewksbury, NJ (US)

( * ) Notice: Subject to any disclaimer, the term of this patent is extended or adjusted under 35 U.S.C. 154(b) by 995 days.

(21) Appl. No.: 12/220,001

(22) Filed: Jul. 21, 2008

Related U.S. Application Data (60) Provisional application No. 60/961,340, filed on Jul. 21, 2007.

(51) Int. Cl.
*A61N 5/067* (2006.01)
(52) U.S. Cl. .............. 607/89; 607/88; 128/898
(58) Field of Classification Search ......... 606/8–13; 607/88–89
See application file for complete search history.

(56) References Cited

U.S. PATENT DOCUMENTS

| | | | |
|---|---|---|---|
| 775,134 A | 11/1904 | Gillette | |
| 4,232,678 A | 11/1980 | Skovajsa | 128/395 |
| 4,388,924 A | 6/1983 | Weissman et al. | 128/303 |
| 4,511,249 A * | 4/1985 | Frungel et al. | 356/5.07 |
| 4,592,353 A | 6/1986 | Daikuzono | 128/303.1 |
| 4,608,978 A | 9/1986 | Rohr | 128/303.1 |
| 4,617,926 A | 10/1986 | Sutton | 128/303.1 |
| 4,760,257 A * | 7/1988 | Pollack et al. | 250/330 |
| 4,905,690 A | 3/1990 | Oshiro | 128/395 |
| 4,930,504 A | 6/1990 | Diamantopoulos et al. | 128/395 |
| 5,040,187 A | 8/1991 | Karpinski | 372/50 |
| 5,259,380 A | 11/1993 | Mendes | 607/115 |
| 5,464,436 A | 11/1995 | Smith | 607/89 |
| 5,549,660 A | 8/1996 | Mendes | 607/88 |
| 5,556,612 A | 9/1996 | Anderson | 424/59 |
| 5,595,568 A | 1/1997 | Anderson | 606/9 |
| 5,640,978 A | 6/1997 | Wong | 128/898 |
| 5,728,090 A | 3/1998 | Martin | 606/3 |
| 5,735,844 A | 4/1998 | Anderson | 606/9 |
| 5,743,901 A | 4/1998 | Grove | 606/9 |
| 5,871,521 A | 2/1999 | Kaneda | 607/89 |
| 6,096,029 A | 8/2000 | O'Donnell, Jr. | 606/9 |
| 6,273,885 B1 | 8/2001 | Koop | 606/9 |
| 6,290,713 B1 | 9/2001 | Russell | 607/88 |
| 6,471,716 B1 | 10/2002 | Pecukonis | 607/89 |
| 6,494,900 B1 | 12/2002 | Salansky | 607/89 |

(Continued)

FOREIGN PATENT DOCUMENTS

EP 1341275 A2 9/2003

OTHER PUBLICATIONS

Nakamura et al. High-Power, Long-Lifetime InGaN Multi-Quantum-Well-Structure Laser Diodes, Aug. 1997, Jpn. J. Appl. Phys. vol. 36 pp. 1059-1061.*

*Primary Examiner* — Henry M Johnson, III
(74) *Attorney, Agent, or Firm* — Matthew J. Hodulik (57) ABSTRACT

Semiconductor diode lasers are tiny sources of light powered by electricity. These are used extensively in medical and aesthetic applications. This patent application covers the concept of replaceable laser diodes for a wide range of applications. Historically, the high power laser sources have been prohibitively expensive to contemplate such an idea. However, as technology advances the price per Watt continues to fall dramatically. Somewhat analogous to the Gillette safety razor concept, this patent application describes how diodes can be replaced in a manner akin to the ordinary razor blade. Simply put, this invention describes replaceable laser light sources for aesthetic and medical applications.

28 Claims, 6 Drawing Sheets

U.S. PATENT DOCUMENTS

| | | |
|---|---|---|
| 6,605,080 B1 | 8/2003 | Altshuler ............................ 606/3 |
| 6,659,999 B1 | 12/2003 | Anderson ........................... 606/9 |
| 6,663,659 B2 | 12/2003 | McDaniel ........................ 607/88 |
| 6,918,922 B2 | 7/2005 | Oron ................................. 607/89 |
| 7,118,563 B2 | 10/2006 | Weckwerth ........................ 606/9 |
| 2002/0151887 A1 | 10/2002 | Stern ................................ 606/41 |
| 2003/0032950 A1* | 2/2003 | Altshuler et al. .................. 606/9 |
| 2003/0189831 A1* | 10/2003 | Yoneda .......................... 362/294 |
| 2004/0136427 A1* | 7/2004 | Hashimoto et al. ............. 372/46 |
| 2005/0106710 A1* | 5/2005 | Friedman et al. ........... 435/287.1 |
| 2005/0135093 A1* | 6/2005 | Alexanderson et al. ...... 362/227 |
| 2006/0007012 A1* | 1/2006 | Machi et al. ............. 340/815.45 |
| 2006/0129211 A1* | 6/2006 | Canitano et al. ................. 607/89 |
| 2006/0149343 A1* | 7/2006 | Altshuler et al. ................ 607/90 |
| 2006/0178714 A1* | 8/2006 | Carullo et al. ................... 607/89 |
| 2007/0070297 A1* | 3/2007 | Matic-Vujovic et al. ........ 353/37 |
| 2007/0179573 A1* | 8/2007 | Laurent ........................... 607/89 |
| 2007/0208398 A1* | 9/2007 | Weber .............................. 607/89 |
| 2008/0021528 A1* | 1/2008 | Carullo, Jr. et al. ............. 607/89 |
| 2008/0125835 A1* | 5/2008 | Laurent ........................... 607/89 |
| 2009/0043293 A1* | 2/2009 | Pankratov et al. ................ 606/9 |

* cited by examiner

OPTICAL DERMATOLOGICAL AND MEDICAL TREATMENT APPARATUS HAVING REPLACEABLE LASER DIODES

RELATED APPLICATIONS

The invention claims the benefit of U.S. Provisional Application Ser. No. 60/961,340, filed Jul. 21, 2007.

TECHNICAL FIELD

This invention relates to the fields of: 1) lasers and light sources for photobiomodulation/cold laser therapy, dermatological treatments, and medical treatments, and 2) photonic sources including diode lasers.

BACKGROUND OF THE INVENTION

The notion of self-contained energy based dermatological equipment is a concept that has been gaining momentum as of late. Palomar Medical Technologies Inc., a leading researcher and developer of light-based systems for cosmetic treatments, recently announced that it has become the first company to receive a 510(k) over-the-counter (OTC) clearance from the United States Food and Drug Administration (FDA) for a new, patented, home use, light-based hair removal device. OTC clearance allows the product to be marketed and sold directly to consumers without a prescription.

Syneron Medical and Proctor & Gamble are reported to have signed a joint development agreement for commercialization of Elos™ technology in home use devices for treating fine lines, wrinkles, age and sun spots, and cellulite (see reference in appendix)

Home use photonic systems for hair removal already exist on the market internationally and on the Internet. Most of these systems are based on semiconductor diode lasers. Semiconductor laser diodes are compact, inexpensive, highly efficient converters of electrical energy to narrow bandwidth laser light.

The use of lasers and photonic tools for dermatological and medical treatments is widely accepted today. There are over 50 significant manufacturers of light based photonic tools for aesthetic dermatology utilizing a number of photonic and electromagnetic radiation based tools for a wide range of procedures. Some of these procedures are clinically challenging and will always be performed in a hospital or clinical environment. The majority of aesthetic procedures are, however, very straightforward and will be easily performed in the home environment. Although the term "laser" might have some dangerous connotations, these home based devices will likely prove to be less dangerous than a curling iron, steak knife, or toaster oven.

Another emerging area of medicine is light based photobiomodulation. This is referred to as Low Light Level Therapy or Cold Laser Therapy. This type of therapy addresses a wide range of ailments and is known to increase circulation and reduce inflammation. The use of lasers and photonics tools for Low Light Level Therapy was popularized in Europe many years ago and is an area of growing interest in the US and throughout the world.

SUMMARY OF THE INVENTION

An advance is made over the prior art in accordance with the principles of the present invention that is directed to a new approach for a system and method for using and changing a disposable diode laser chip or bar in a home-use laser device.

In one embodiment of the invention, an apparatus and method are described for performing a laser light treatment, wherein the apparatus includes a handpiece for provision of power to one or more laser diodes and a replaceable laser diode module which couples and de-couples from the handpiece. The laser diode module has an electromechanical interface that enables the laser diode module to be replaceable by an ordinary user and as such the laser diode module is essentially disposable. In another embodiment of the invention, the laser treatment device is operable to give an indication to replace the laser diode module subsequent to the laser diode module reaching a time or degradation threshold.

BRIEF DESCRIPTION OF THE DRAWING

The teachings of the present invention can be readily understood by considering the following detailed description in conjunction with the accompanying drawings, in which.

DETAILED DESCRIPTION

Exemplary embodiments of the invention will now be described while referring to the figures, several of which may be simultaneously referred to during the course of the following description.

An exemplary embodiment of the present invention relates to a skin treatment device that makes use of semiconductor laser diodes. In order to ensure optimal efficiency in skin treatment, the invention assures optimal operation of the laser diodes. The laser diodes of the present invention device are contained in a removable module that may be easily replaced by a user of the device either after the diodes have reached a given operational time period or upon falling below a given operational characteristic threshold, such as, power output, or at a prespecified time of useful life. In accordance with different aspects of the invention, a heatsink for the laser diodes may or may not be included within the replaceable module.

As will be explained, one way in which to implement the invention is to utilize the laser diode technology available today in a counterintuitive manner, wherein the semiconductor laser diodes are operated out of the traditional specified range in order to achieve higher power levels with less material, but with lower lifetimes. Further, once this operating mode is recognized, design optimizations to the diode chips or bars can be implemented to further improve performance and reduce cost.

Light Based Technology

This invention primarily considers laser diodes as they are one of the most efficient sources of converting electrons to photons with narrow spectral emissions. The invention also considers non-laser light emitting diodes (LEDs) and flashbulbs.

Relevant Parameters of Laser Diodes

High power multimode near infrared (NIR) diode lasers are typically based on GaAs substrates with Al—, In—, and/or P— GaAs epitaxial layers grown on the top. Longer wavelength diodes are based on Indium Phosphide or other materials with the desired energy bandgap for the wavelength of choice. A p-n junction is formed that emits light when the diode is electrically energized. The typical size of a diode laser has a cross-section of approximately 1 micron by ten to several hundred microns and a cavity length of less than one millimeter up to several millimeters. A GaAs wafer can accommodate many diode lasers and the wafer can be cut such that multiple lasers remain on a single piece of the substrate. These are referred to as diode bars. Bars can have as few as two or up to over 100 individual lasers. The lasers typically all emit light in the same direction and the individual lasers on the majority of commercial bars are operated electrically in parallel.

Semiconductor Manufacturing Process as it Relates to this Invention

When products are manufactured in higher volumes the cost point falls. Because of the large capital equipment required for the better understood electronic semiconductor manufacturing and the nature of high volume automation, this is an extreme case that demonstrates economies of scale. That is, inherent to the semiconductor manufacturing process, the cost falls dramatically as volume manufacturing is implemented. In quantities of millions, the unit price may be hundreds of times lower than in volumes of hundreds. This same principle holds true for semiconductor laser diodes of the type utilized to implement the present invention, wherein if manufacturing quantities were to be increased to satisfy the need for replaceable diode modules used in significant quantities, then the price of the semiconductor laser diodes could also decrease significantly.

Unlike the highly automated silicon based semiconductor-processing technology, high power laser diodes are currently manufactured with significant human intervention. Once volumes in high power diode laser manufacturing reach the level associated with consumer products, processing will be further automated and costs and prices will fall dramatically.

Diode Laser Lifetime

Diode lasers have finite lifetimes after which the diode becomes less efficient and ultimately dies. This lifetime relates directly to the temperature of the p-n junction. The temperature at the junction and consequently the diode lifetime is determined largely by: drive current, electrical to optical conversion efficiency, and rate of heat dissipation.

Drive Current: Diode lasers typically operate at 2 V per diode delivered from a constant current source. A significant amount of the electrical power provided (e.g. 50%+) is converted to optical energy. The balance of the energy is left as heat.

Electrical-to-optical conversion efficiency: The output optical power relative to the electrical input.

Heat dissipation: The rate at which the heat is removed from the diode junction. This is a very important parameter in the operation of high power laser diodes. It is further a complicated area of study. The actual junction is quite small and the GaAs material is a poor thermal conductor when compared to the material upon which it is mounted, possibly aluminum, copper, copper-tungsten or a copper alloy or combinations of a metal with ceramic.

The output power is directly related to the drive current. After a certain time of operation the diodes start to deteriorate and will ultimately reach a (lower) power level that will be ineffective for most applications. The rate of degradation is nonlinearly related to the temperature, and it follows that the rate of degradation is non-linearly related to power (as pictorially suggested in FIG. 8). A diode laser systems manufacturer optimizes the diode performance in most applications where the power levels correspond to thousands of hours of operation.

By utilizing laser diodes that are optimized for these long hours of operation and manufactured in comparatively low volumes, the costs associated with the diodes can be considered prohibitively expensive for certain lower cost applications such as personal laser dermatological equipment or other personal laser usage.

A rule of thumb in the diode laser field is that the lifetime of a diode laser relative to its power output is as follows.

$$T_{hpo} = T_{lpo}[P_{high}/P_{low}]^5$$

where, $T_{hpo}$ = lifetime of the diode operated at high power
$T_{lpo}$ = lifetime of the diode operated a low power
$P_{high}$ = high power level (W)
$P_{low}$ = low power level (W)

This highly nonlinear relationship drives the industry to operate the diodes at thousands of hours of operation. However, if an application only needs a few hours of operation the diodes can be driven very hard and still meet the needs of the application. In some business models, the notion of replacing these diodes may also be considered an advantage.

Spectral Properties of Diode Lasers

Diode lasers operate effectively and at high powers from 620 nm-1900 nm and can be made to operate as short as 370 nm and out to 3000 nm. They deliver light in a band from 1-50 nm, typically in the near IR 2-15 nm. In medical applications, various wavelengths are selected to match the target chromophor in tissue. Because of their narrow emission bands compared to LED's and lamps, they are well suited to target specific tissue chromophors including melanin, water, blood or sub-cellular features.

This invention contemplates diode lasers from 620 nm-3000 nm and applications of these wavelengths will be discussed below.

Thermal Properties of Diodes

Diode lasers are electrically connected to their power source by an anode and a cathode. Unlike some electronic components, the anode and cathode of the high power diode laser must not only be designed to accommodate the high current draw of the diode itself, but also be designed as the heat sink of the diode. The diode lasers themselves are so small that if they were to transfer their heat only through convection to the air they would be limited to extremely low powers. Therefore, the electrodes are designed to also dissipate the waste heat generated.

The diode lasers contemplated herein must be in intimate contact with high thermal conductivity electrodes likely made from aluminum, copper or a copper alloy in order to provide the required heat dissipation. The diodes can either be soldered to a copper electrode/heat sink or mechanically coupled (e.g., clamped) to the electrodes/heat sink.

Operation at High Temperature

Fundamental to the laws of thermodynamics, the rate of heat transfer from one material to another or within a material is governed by complex partial differential equations in space and time but is proportional to the thermal conductivity of a material and the difference in temperature, "delta T" or ΔT. Aluminum, copper or copper based alloys generally meet the needs of having high electrical and thermal conductivity and this is known. One aspect of the invention contemplates diodes operated at as high a temperature as possible to meet the operational requirements, and as such this will create the greatest ΔT and consequently demonstrate the greatest rate of heat removal. In this case, one exemplary embodiment will have a diode temperature in excess of 50 degrees C. It is unusual that diode lasers operate at these high temperatures because this has adverse effects on the diode lifetime.

Series Operation

High power diode laser bars are a set of diode lasers on one piece of semiconductor material. The diodes are all aligned beside one another making it relatively straightforward to connect them with a single electrode and operate them electrically in parallel. This works quite nicely for existing long lifetime applications of laser diodes. In general though, high current 2 V sources are quite expensive compared to high voltage, low current sources of the same power. A 2 V 50 amp (e.g., high current) source delivers 100 Watts of power but is much more expensive than a 20 V, 5 amp source delivering the same 100 W.

The cost drivers for the compatible diode lasers themselves are contrary to the above electronics driver cost models. The diode lasers are more inexpensively made as bars and operated in parallel, as each diode requires 2 V at constant current. Although in many cases high power diode lasers are made in stacks of bars and each bar is operated electrically in parallel, but the bars themselves are in series. The notion of running single emitters in series goes quite contrary to the cost model of diode manufacturing. There is significant extra effort in dicing the bars into single emitters and then reconnecting them in series. This extra effort, however, once put in the context of the entire system, will be much less than the differential cost of the driver. As stacks of single emitters go to higher volumes the economic advantage will be even more pronounced.

Figure 1:
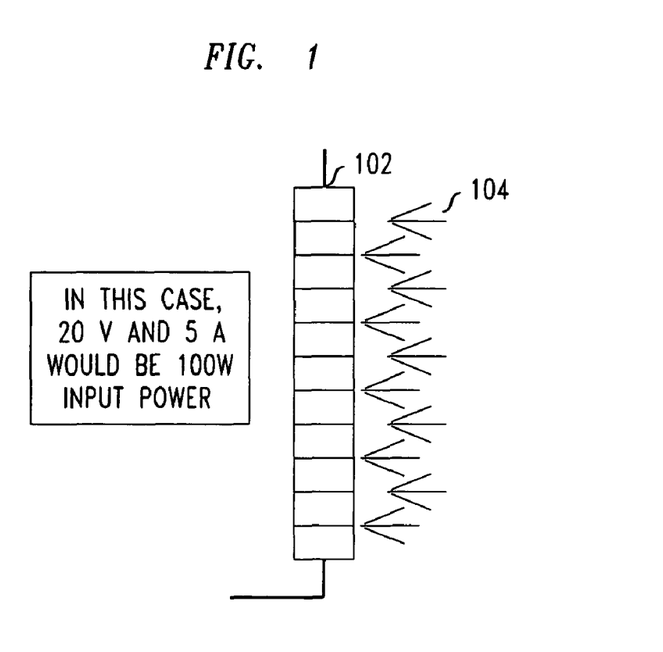
FIGS. 1, 1A and 2 show exemplary embodiments of electrically serially packaged laser diode chips or bars.
Figure 1A:
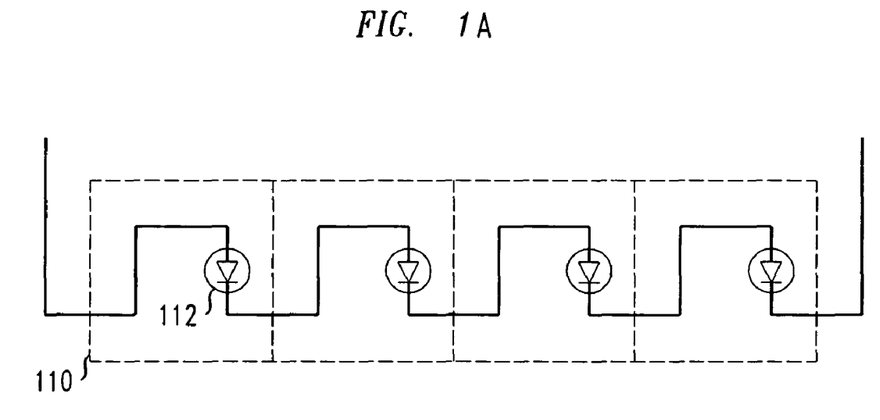
Figure 2:
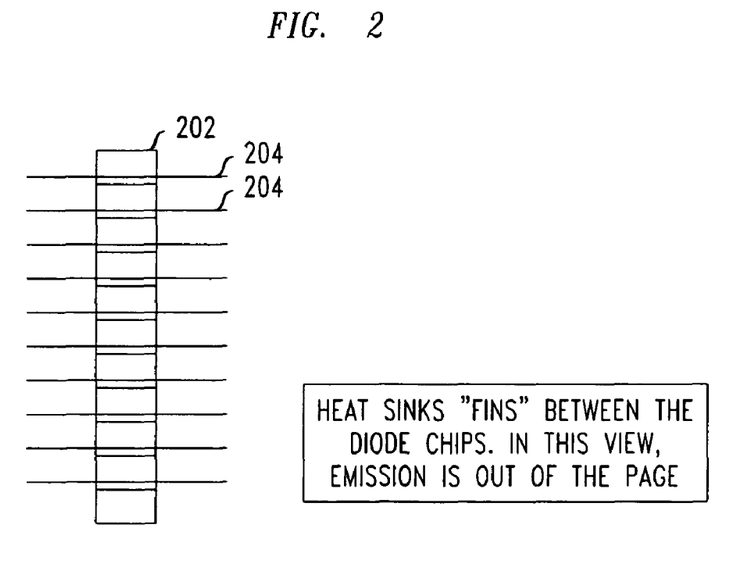

It therefore is contemplated herein to make removable or replaceable diodes for dermatological or medical applications where two or more diodes are used. For three diodes, the voltage is then >5 V (e.g., 2 V/diode×3 diodes=6 V.) FIG. 1 shows 10 (ten) diode chips 102 placed in series, where a roughly 20V power supply provides 5 (five) amps of current and an input of 100 Watts. Emission from the diode chips is represented as output 104. FIG. 1A shows a generalized circuit for four diode chips 110 placed in series. As can be seen, each of the diode chips includes a semiconductor laser diode 112 that is electrically coupled in series with another laser diode. It would be understood that other electrical components (not shown) may also be included within the electrical circuit of each diode chip 110, e.g. resistive elements, etc., in order to facilitate proper operation. FIG. 2 shows the same stack of laser diodes 202 placed in series and having heatsinks 204 placed between each of the diode chips.

Rough dimensions for the above, may be, for example, cavity length 1-2 mm, package length in that dimension 1-4 mm. Package in depth in left figure above and width in the right figure, 1 mm wide (typical diodes might be in the range of 100-300 microns wide), the height of this package will depend upon the number of single emitters and also the thickness of the solder and fins. This package will be roughly 1-2 cm tall. With more diodes it could be 3 cm tall. An example of how the diodes could be mounted is described in U.S. Pat. No. 5,040,187 to Karpinski, the content of which is incorporated herein by reference. A similar approach to stacking bars can also be used to stack single emitters. Although the above described embodiment describes application of the present invention in connection with diode chips placed in series, it would be understood that the replaceable diode module aspect of the present invention would also operate in connection with parallel packaged diode chips, assuming a suitable power supply.

Power Supplies

Figure 3:
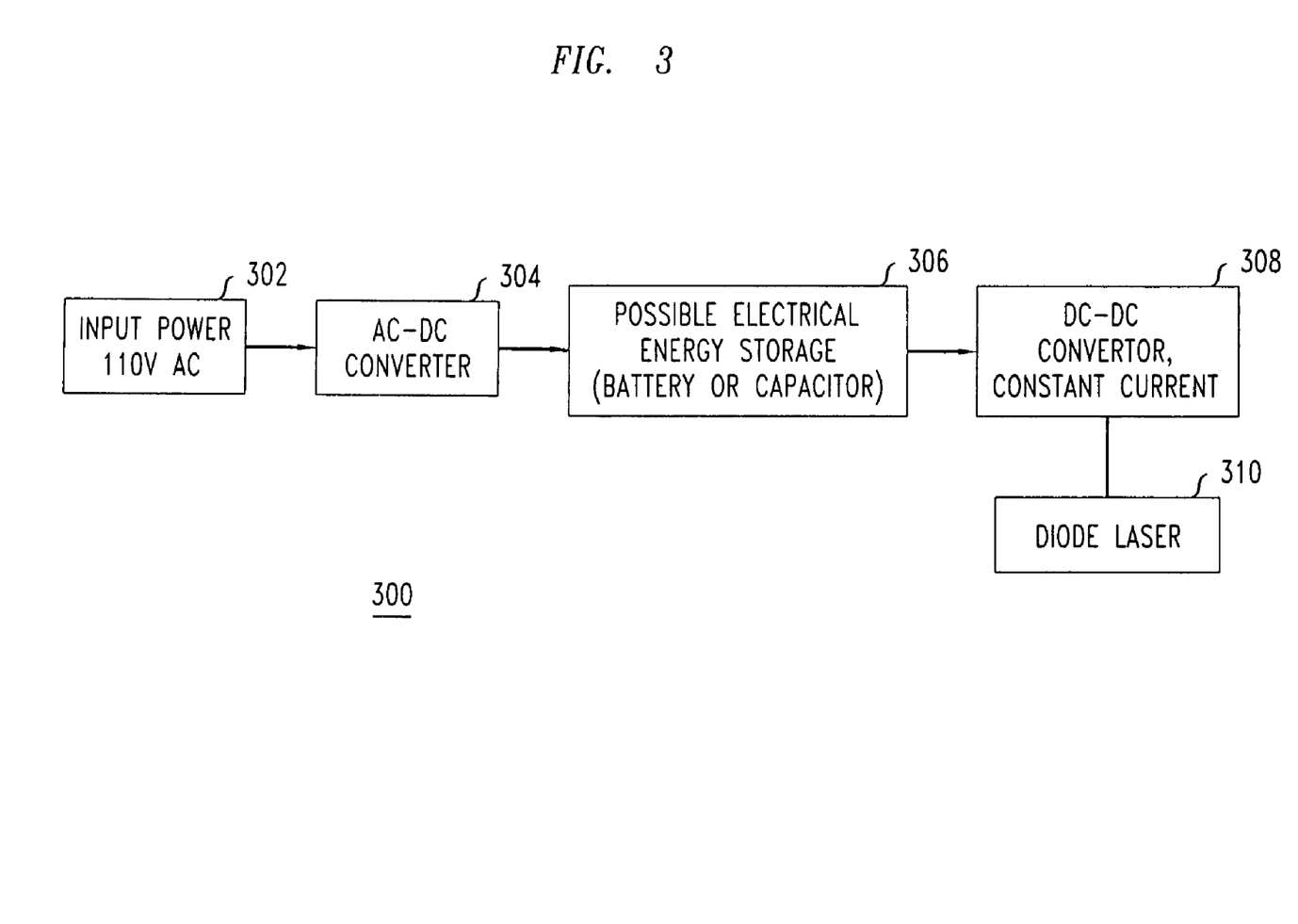
FIG. 3 shows one exemplary embodiment of power supply for use in connection with the principles of the present invention.

The power supplies for the series packaged diode lasers need to operate at approximately 2 V per diode laser. As described above, the use of lower current power supplies may have a significant advantage for implementation of a device having replaceable diode modules. FIG. 3, shows one possible implementation of a power supply 300 useable for implementation of the present invention. More specifically, the power supply receives input AC power 302 (110 or 220V) at an AC-DC converter 304. The output from the AC-DC converter may couple to and assist with charging an electrical storage device 306, such as a battery or capacitors. The electrical storage device 206 (or AC-DC converter) in turn couple to an optional constant current DC-DC converter 308 which powers the laser diode 310. Since in some applications the diode lifetime may be very short, it is possible that a constant voltage would be adequate.

Replaceable Laser Diodes

This invention contemplates two approaches to a replaceable laser diode: replacing the semiconductor piece itself or replacing the semiconductor piece with its electrodes providing mechanical support and the local heat sink. A "semiconductor piece" can be either a single piece of semiconductor with a single laser or single piece of semiconductor with multiple lasers on it.

Figure 4:
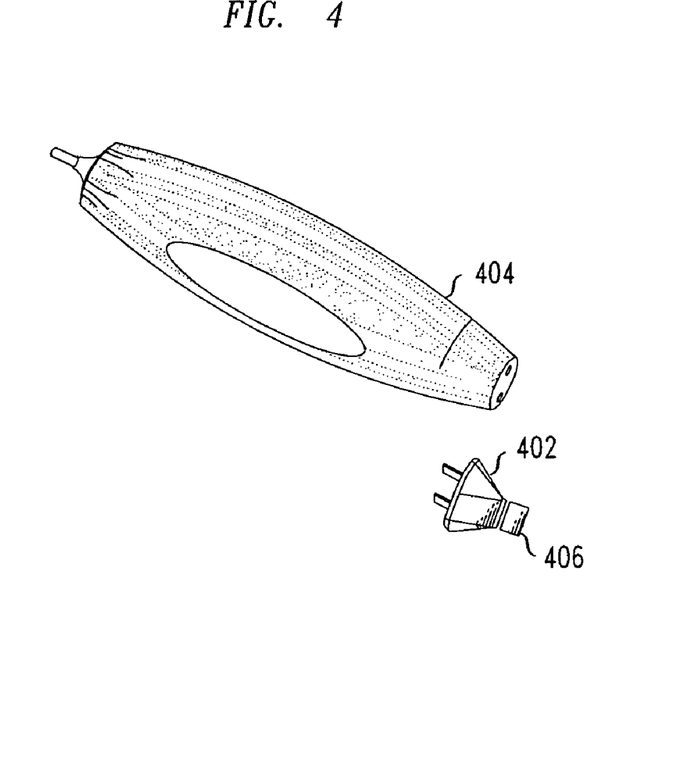
FIG. 4 shows one exemplary embodiment of a handheld laser treatment device having a replaceable laser diode module.

Referring to FIG. 4, in an exemplary embodiment, the diode laser, mounting, and local thermal heat sink will be self-contained within a replaceable module 402 that attaches to a handpiece 404. Collimation or scattering optics 406 are figuratively represented which may or may not be part of the replaceable module. The invention also contemplates the replacement of the diode and any additional related components, wherein these other components might include any optics between the laser and the skin, electrical components coupling to the handpiece 404, as well as other components that one skilled in the art may consider to be advantageously included within the replaceable module. Other characteristics of a personal dermatological treatment device, besides that of the replaceable laser diode module, would be similar in fashion to that of the Weckwerth patent (U.S. Pat. No. 7,118,563), the entire contents of which are incorporated by reference herein. Such other characteristics may include, but not be limited to, the power mechanisms, handheld body, charging mechanism, interlocks, etc.

As would be understood by a person skilled in the art, the details of an interface between the replaceable module and the housing to which the module attaches would be dependant upon the power level of the replaceable module. Such an interface would also provide adequate current carrying capacity for an electrical interface, provide the necessary mechanical stability, and provide suitable thermal coupling for heat dissipation.

Figure 5:
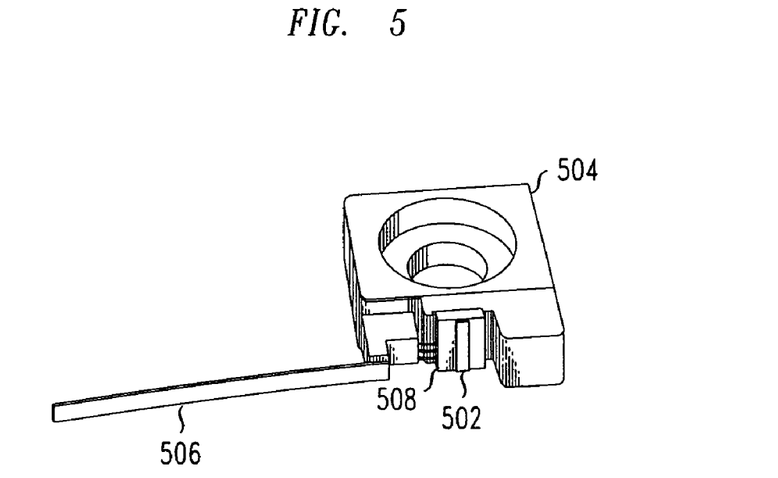
FIG. 5 shows one exemplary embodiment for a diode and heatsink mounting methodology.

Referring to FIG. 5, an example of diode and heatsink mounting methodology shows a diode laser 502 soldered to a heatsink 504, which will provide mechanical stability to the semiconductor device, electrical conductivity, and a thermal heatsink. An example of an open heatsink single emitter is an industry standard C-mount (shown in FIG. 5 and commercially available from nLight, www.nlight.net or Coherent, Inc. http://www.coherent.com/lasers/ index.cfm?fuseaction=show.page&ID=854&loc=343) with a single emitter semiconductor or a single semiconductor with multiple emitters. Electrode 506 and submount 508 are also shown. The C-mount shown in FIG. 5 is just an example of a commercially available open heatsink. In practice, a custom designed and simpler embodiment would be appropriate. In some cases, the thermal loading will be reduced from conventional CW (continuous wave) operation requirements because these diodes will be operating in a pulsed mode with ms pulses. A customized mount with large anode or cathode may also be used to allow for heat dissipation through typically one of the electrodes.

In an exemplary embodiment of the invention, the replaceable diode laser will have the electrical and thermal capabilities shown in the example of FIG. 5, but also have a mechanical interface to allow a user to change the diode and local heat sink.

Figure 6:
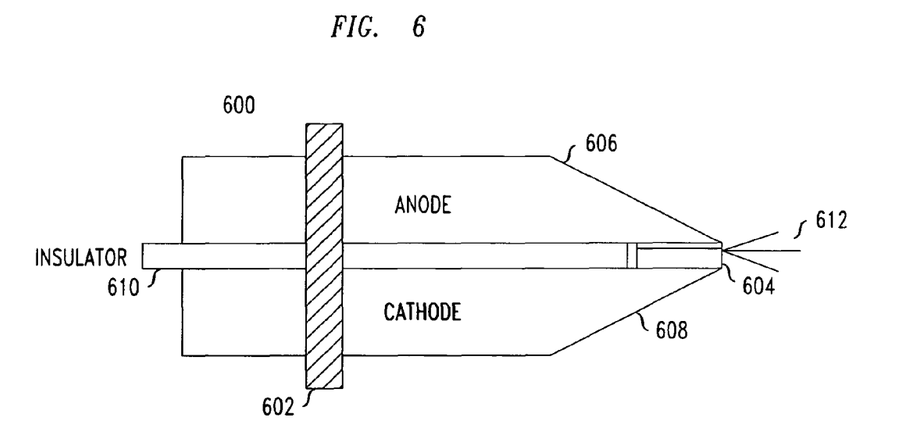
FIGS. 6 and 7 show two exemplary mounting methodologies for a replaceable laser diode bar in accordance with principles of the present invention.

In another exemplary embodiment, the replaceable diode laser is clamped into the device. The semiconductor laser device will be sold with a disposable plastic or paper holder. The semiconductor laser will be fixed into the holder and then clamped into place. (See for example, FIG. 7.) In a practical sense, it is challenging to get as efficient of an electrical or thermal contact as soldering. However, the clamping connection provides the advantage of avoiding problems associated with the thermal expansion mismatch of the solder to the semiconductor material. This will much more easily allow higher temperature operation. General clamped laser diodes may be purchased from Monocrom, SL of Vilanova, Spain. (www.monocrom.com). FIG. 6 shows a figurative illustration of a clamped diode bar 600. A nylon clamping screw 602, for example, can be loosened to remove the diode chip 604 which is positioned between the anode and cathode electrical contacts 606, 608 from a power source. The anode and cathode electrical contacts are separated by an insulating material 610 in order to provide uniform spacing for the diode chip 604 as it is located between the electrical contacts 606, 608. An emission 612 is also shown from the diode chip 604.

A lever or thread (as shown in FIG. 6) would be designed to offer a mechanical advantage and in such a way so as to provide optimal pressure for the clamping approach. In order to provide adequate electrical and thermal conductivity, a thin layer of malleable metal may be affixed to the diode bar or to the electrodes.

Figure 7:
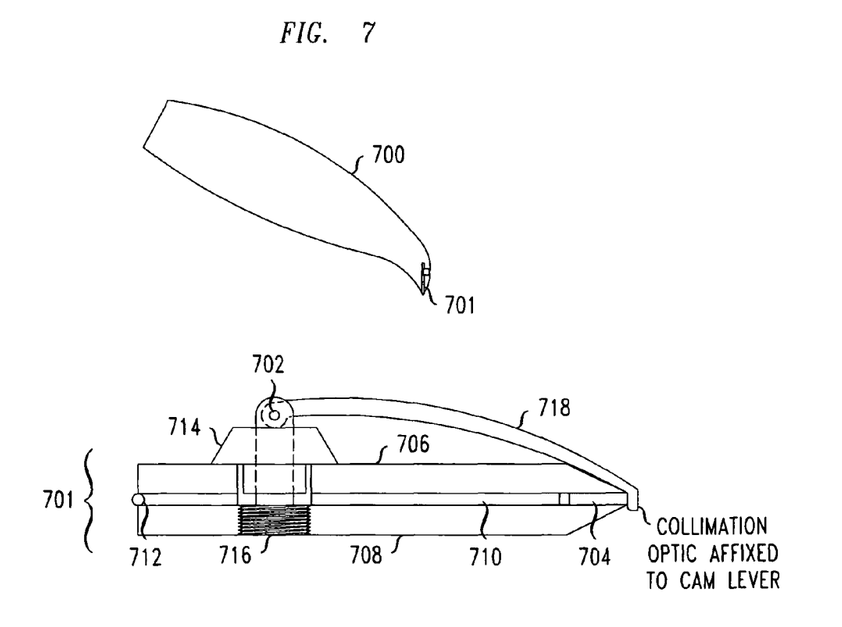

Referring to FIG. 7, an alternative exemplary embodiment is shown for a clamping mechanism 700 for holding a disposable laser bar in accordance with one aspect of the present invention. As shown, the clamping mechanism 700 uses a cam lock 702 to hold a laser diode bar 704 in place between an anode and cathode contact 706, 708. The anode and cathode are separated by an insulating material 710 and an insulator fulcrum 712 to provide a specified gap between the anode and cathode 706, 708. The cam lock pin 702 is a hinging point for the lever 718. A screw 716 is threaded into the cathode 708, passes through bushing 714 and also attached to the cam lock pin 702. Once the lever 718 is lifted it will release the clamping compression between the anode and cathode. This will allow the disposable semiconductor bar or chip to be removed and replaced. A new semiconductor laser can then be replaced within the unit between the anode and cathode. The cam lock 702 can then be re-engaged to securely lock the laser in place between the anode 706 and cathode 708. As shown, a collimation optic is also affixed to the cam lever 718.

The diode bar must be critically aligned to the heat sink and electrodes so the semiconductor itself or the plastic or paper mount with which it is sold would need to have alignment features such as holes for alignment pins or other adequate alignment designs. Although not shown in the drawing, it is understood that this would need to be a high-resolution alignment process.

A similar architecture could be used in replacing a single emitter or stack of single emitters shown in FIGS. 1 and 2. And again, it would be similar to replacing a diode bar or single emitter that is pre-mounted to a heat sink. This would provide the substantial advantage of requiring a much less critical alignment as the local electrode and local heat sink would be affixed at the factory.

The single emitter diode laser, a single emitter diode laser on a heat sink, a diode laser bar, diode bar and heat sink or single emitter stack would be replaced by the end consumer.

Indium and Copper

Indium is a malleable metal that can be used as a solder to attach a semiconductor diode laser to a heatsink. Indium is referred to as a "soft solder" and at times in high power applications disadvantageously leaks or loosens from the bonding area and interferes with the diode laser output surface, often times causing failure.

Copper is recognized as a good thermal conductor. However, although it has good thermal parameters and is very inexpensive relative to alternatives, it is not often used as a heat sink for high power diode lasers. One drawback of copper is that solders compatible with copper are generally soft solders and can, over time and through thermal cycling, come out from the bonding area and interfere with the laser.

Because only very low lifetimes are required by the invention, the idea of copper heat sinks with soft solders, historically discounted in high power diode applications, could now be very appropriate to applications involving removable or disposable diodes.

One of the major challenges faced by diode design engineers relates to lifetime. The notion of a use for ultra-low lifetime diode lasers that can be replaced will provide the engineers the ability to implement significant cost savings approaches at the expense of lifetime.

In accordance with the present invention, the laser diodes that will be operated at current levels greater than their long-lifetime levels will be housed in a replaceable module that will be part of the personal laser dermatological/medical device. Even though the laser diodes in the replaceable module would be overdriven such that their usable lifetime would be significantly reduced (compared to conventional wisdom) over long lifetime levels, the average operational lifetime for such modules would still be at levels that are envisioned to be satisfactory to the consumer—assuming a reasonable price point for the replaceable modules is achieved. This lifetime is expected to be in the range of minutes to hours depending upon the application. For example, if a laser bar were operated at 50 W for 50 ms delivering light over a spot with an area of 0.25 square centimeters, it could treat an area of 12.5 cm×12.5 cm with 625 pulses. This would be a reasonable treatment area for hair removal on a bikini line, underarm, or other small area. This would only consume 31 seconds of the diode lifetime. Consequently, one could envision a complete diode lifetime of five minutes, ten such treatments, as being useful. For other applications, these may be single use; a fraction of a second total lifetime may be perfectly acceptable in some market scenarios.

Although one methodology for implementation of the present invention describes overdriving currently available laser diode technology, one could also utilize lower quality diodes that last for a shorter relative time compared to state-of-the-art diodes. Thus, these less costly materials could also be used in order to make the replaceable diode module scheme of the present invention practical.

Applications and Clinical Indications

Home use laser dermatological equipment in accordance with the present invention can be either battery powered or powered by 110 or 220 VAC from a wall plug. See for example, those corded systems produced by Ya-Man Ltd. of Tokyo, Japan. As stated previously, an aspect of the present invention is to use what would historically be considered an over-driven diode that is replaceable. This can be a single emitter diode, multiple single emitters, a diode bar or array including two or more emitters, or multiple bars or arrays. In addition, with the idea of reducing the current and increasing the voltage above the standard nominal 2 V required by each individual diode, a set of diodes can be operated in series.

There are different applications of consumer diode lasers and different producers of these devices will position the product at different power levels in accordance with an efficacy vs. cost and safety trade-off curve. It will be advantageous in developing a business strategy that the diode lasers operate in a high power mode, yet have a reduced lifetime. Diode technology has progressed very rapidly allowing an increase in power from a given diode size. A technologist might suggest that these improvements provide an increase in reliability. Another perspective, however, would be to fix the reliability and power, resulting in the same performance from a smaller, less expensive device. Or, by manipulating the trade-off space in a desirable direction, reduce the reliability substantially, increase the power and select the optimal device size.

With respect to laser based dermatological treatment devices, the radiant exposure applied to the skin (often referred to as "fluence", expressed in Joules per square centimeter) by this class of devices is typically in the 10-40 J/cm$^2$ range for laser hair removal, The wavelength is typically near 800 nanometers. In the mid-late 1990's studies with professional laser systems showed that pulse durations in the 3-30 ms range were optimum. Subsequent studies showed that longer pulses (up to at least several hundred milliseconds) can quite effectively achieve hair-regrowth inhibition, and can also reduce epidermal heating for a given fluence when a heat conduction path is provided (e.g., by incorporating an output window made of sapphire in contact with the skin or other forms or skin cooling). Commercial professional systems have been based on this longer pulse approach including a device manufactured by Canadian based, OpusMed and a device manufactured by Palomar (SLP-1000).

Single bar laser diodes have been demonstrated with powers of >700 W. At fluences of >15 Joules per cm$^2$ permanent hair removal has been demonstrated. Commercially available single bars are specified at nominally 100 W with 10,000-hour lifetimes with active cooling. Much higher powers can be achieved with these same diodes by sacrificing, what in this case is unnecessary lifetime. With these higher powers, a handheld consumer device can be made for not only hair regrowth inhibition, but hair removal more akin to what is used with professional hair removal lasers.

Aesthetic Dermatology Laser Removal

The primary method of laser hair removal is based on selective differential absorption between the melanin and other tissue absorption. Melanin is heavily absorbed by wavelengths in the near infrared (NIR). Most other components of tissue scatter this light but absorb less. Hair follicles are typically darker due to their large melanin concentration. Thus, hair follicles are heavy absorbers of NIR radiation. With the correct match of wavelength and pulse duration a hair follicle will absorb the light and increase in temperature. If the temperature reaches 70 degrees C. for several milliseconds it will be damaged or killed. This will lead to a delayed regrowth or in the optimal case, no regrowth at all. There may be other nearby dormant hair follicles that grow back providing the appearance of regrowth, however, under optimal treatment parameters the particular hairs targeted will not regrow at all. In some cases also when hair is treated at a fluence lower than that required for permanent reduction, a positive effect occurs allowing regrowth of a hair that is much lighter and thinner. Such a hair is aesthetically preferred to the darker hairs allowing less painful shaving or less noticeable hair.

For the sake of this discussion we will assume a 100 W diode output for an exemplary home use system. This is quite low relative to professional systems today, although there are some professional systems that do not even output this high of power levels. The 100 W output level is quite high, however, relative to low end systems that are available today on the internet. And it is comparable to high end home-use systems sold internationally. With regard to output power, this exemplary 100 W could be achieved, for example, with 10 diodes of 10 W each, 20 diodes of 5 W each or 40 diodes of 2.5 W each. The level of fluence needed for efficacious treatment for permanent hair removal is about 15 Joules/cm squared. At 100 W operated for 30 milliseconds, this would correspond to a spot size as described in Table 1

TABLE 1

Moving downward on the table increases efficacy and simultaneously increases theoretical risk to the consumer/patient. 100-500 ms pulses also can be used effectively.

| Average Power (watts) | Pulse duration (ms) | Spot size (square cm) | Energy (Joules) | Fluence (J/cm2) | Comments |
|---|---|---|---|---|---|
| 100 | 20 | 0.5 | 2 | 4.0 | Fluence low for treatment |
| 100 | 40 | 0.5 | 4 | 8.0 | Adequate for darker skins for hair re-growth inhibition |
| 100 | 60 | 0.5 | 6 | 12.0 | Good for hair re-growth inhibition |
| 100 | 80 | 0.5 | 8 | 16.0 | Good treatment for hair management and some permanent |
| 100 | 100 | 0.5 | 10 | 20.0 | Permanent hair reduction |

The dermatological and medical treatment device of the present invention is applicable for a number of uses including hair removal, as has been discussed. Other applicable treatments, besides that of hair removal include laser treatment for acne, the reduction in the appearance of cellulite, wrinkle treatment, and pigmentation altering. This would be understood by those skilled in the art and is already broadly used in professional systems. The wavelength and power level would be optimized for each specific application.

Figure 8:
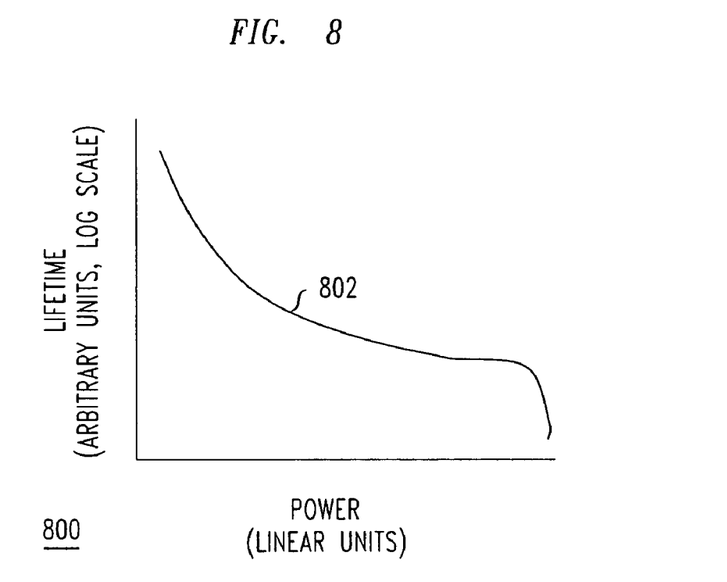
FIG. 8 is a graph of laser diode lifetime versus applied power qualitatively demonstrating a non-linear relationship.

Referring to FIG. 8, a graphic illustration 800 is shown for power versus lifetime for a traditional semiconductor laser. The plot 802 shows generally that the lifetime of a laser diode decreases significantly as power is increased until a point of catastrophic failure. The plot illustrates a strongly nonlinear inverse relationship between operating power and lifetime of the diode and should not be interpreted quantitatively.

Figure 9:
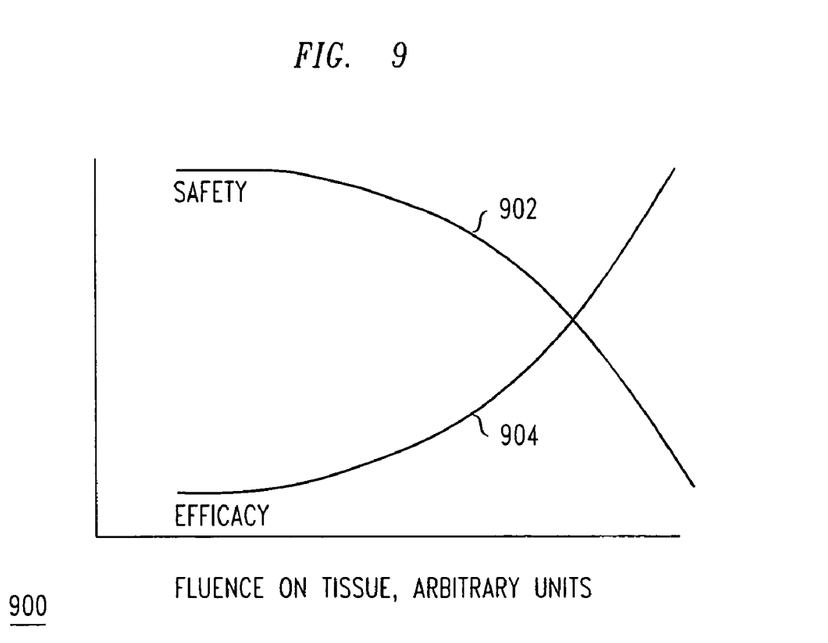
FIG. 9 is a graph showing qualitative trends for power versus fluence for two parameters relating to dermatological treatment.

Referring to FIG. 9, another graph 900 that includes plots Safety 902 and Efficacy 904 and shows generally that as laser power/fluence increases, the laser becomes less safe and can potentially cause more side effects and as the laser power increases (and particularly in the ranges suggested herein) the laser becomes more efficacious. Again, this model has limitations and is not always true for all indications, but generally, over some range, as fluence increase efficacy goes up and the risk of side effects also goes up.

In a home-use product, the greatest efficacy may not be the optimal efficacy. The greatest lifetime will not be the optimal lifetime. And the safest power level will not be the optimal power level. The business, clinical and regulatory experts can select based on knowledge of optimizing the business concerns, clinical objectives of a product, and meeting government regulations. This invention contemplates and provides instructions for the engineers to design a product to meet these needs over a very wide range of product configurations.

As is understood by those skilled in the art, for many indications optimal treatments using laser diode devices take place when the skin that has been contacted by the laser light is able to be cooled pre-treatment and/or soon thereafter. In accordance with the present invention, a skin cooling function can be integrated with a handheld device with replaceable laser diodes. This could take the form of a thermo-electric cooler that contacts the skin. It could also be designed in such a way that ice is used. The present invention device would include an attachment that accepts various kinds of pre-made ice cubes or in the alternative would be sold with an "ice cube tray" or Popsicle maker that is used as the attachment to accept the ice that is then used as the skin cooler. The user would freeze and then connect a large ice cube into the device. When a user performs the hair removal treatment, they attach the "Popsicle stick" attachment to the device where the ice cube is in contact with the skin pre-treatment. It is particularly important to have integrated skin cooling when darker skins are being treated.

As would be appreciated by someone skilled in the art, it is also suggested here that a thermal and optical coupling gel (clear ultrasound gel or other water based gel) be applied to the skin pretreatment to help remove heat from the surface of the skin.

Photobiomodulation

The field of professional light sources for photobiomodulation is much smaller than the dermatological area from a financial standpoint. Although there have been over 2000 scientific studies in this field, many of which demonstrated compelling results, there is still wide range of accepted treatment dosages, treatment protocols and product configurations.

The concept of photobiomodulation (used essentially interchangeably with photobiostimulation herein) relates to light interacting at the cellular level and effectively giving instructions to the cells to perform certain functions. It is believed that the light interactions with the mitochondria in the cell and signals certain cells to be energized. One theory is that the laser relaxes the smooth muscles. In the case were the light relaxes the smooth muscles surrounding capillaries this process can increase circulation. Further, it can relax the muscles around the lymphatic vessels and thereby increasing lymphatic system activity and reducing inflammation. Although the mechanism of action is a point of debate in the field, it is clear that the laser based photobiostimulation does reduce inflammation and this fact alone has broad reaching implications.

The first publications about photobiostimulation appeared more than 30 years ago. In 1960's and 1970's researchers in Eastern Europe, the Soviet Union and Hungary, actively developed photobiostimulation. Numerous early studies attributed the positively results to the coherent and polarization properties of laser radiation. Although it is likely that laser radiation provides deeper penetration and consequently more targeted illumination than alternative light sources, recent studies have shown that the cellular response to light is not dependant upon the coherent or polarization properties of the radiation. Although this theory is still believed by many users, it is often considered outside the mainstream medical practices.

It is clear now that photobiostimulation can not be considered separately from physiotherapeutic methods like low frequency pulsed electromagnetic fields, microwaves, time-varying or static magnetic fields, focused ultrasound, direct-current electricity, etc.

By the dawn of the 21st century a certain level of development of light therapy based on cellular interaction had been achieved. In photobiostimulation, the question was no longer whether light has biological cellular effects but rather how radiation from therapeutic light sources works at the cellular and organism levels and what are the optimal light parameters for different uses of these light sources.

Direct activation of various types of cells via light absorption in mitochondria is one way that the light interacts with the cells. Primary photoreceptors and mechanisms of light interaction are not thoroughly understood but the effects have been demonstrated in numerous studies.

The vast majority of photobiostimulation is related to superficial external applications because 1) it is easier from a regulatory and safety standpoint to perform noninvasive trials and 2) many wavelengths that trigger the cellular photoreceptors do not penetrate tissue deep enough for significant cellular response.

Clinical applications of photobiostimulation are diverse and will be significantly broadened by the inventions herein. Photobiostimulation is used by physiotherapists (to treat a wide variety of acute and chronic musculoskeletal aches and pains), by dentists (to treat inflamed oral tissues, as an anesthetic, and to heal diverse ulcerations), by dermatologists (to treat edema, indolent ulcers, burns, and dermatitis) by rheumatologists (to relieve pain and treat chronic inflammations and autoimmune diseases), and by other specialists as well as general practitioners. Photobiostimulation is also used widely in veterinary medicine (and especially in race horse trainers) and in sports medicine and rehabilitation clinics (to reduce swelling and hematoma, relieve pain, improve mobility, and treat acute soft tissue injuries). Light is applied directly to the respective areas (e.g. wounds, site of injury) or to various points on the body (acupuncture points, muscle trigger points).

Clinical applications of photobiostimulation are diverse. The field is characterized by a variety of methodologies and uses of various light sources with different parameters (wavelength, output power, continuous or pulsed modes, and pulse parameters). In recent years, longer wavelengths and higher output powers, presumably associated with deeper penetration depths, have been employed.

In addition to the conventional utilization of photobiostimulation, this invention contemplates much broader implications in areas of medicine including: urology, ophthalmology, cardiology, orthopedics, and aesthetics. Often times in these fields the professional laser products utilize disposable fiber optics. Given certain scales of economy, these could be offered to provide disposable diode lasers and fiber optics. This would provide the clear advantage of having a new and calibrated laser for each procedure. It would further provide the advantage of spectral versatility in one product platform.

Laser light is primarily administered directly by professionals in the respective medical fields but once the treatment is better understood the light may be prescribed like medications are now. The ideas suggested herein will enable certain home-based treatments and allow for specific cumulative dosages to be provided by prescription only.

Photobiological reactions involve the absorption of a specific wavelength of light by the functioning photoreceptor molecule. The photobiological nature of low power laser effects means some molecule (photoreceptor) must first absorb the light used for irradiation. After promotion of electronically excited states, primary molecular processes from these states can lead to measurable biological effect at the cellular level. Studying action spectra of the absorbers can identify molecular photoreceptors.

The first action spectra in visible-light region were recorded in the early 1980's for DNA and RNA synthesis rate, growth stimulation of *Escherichia coli* and protein synthesis by yeasts for the purpose of investigating the photobiological mechanisms of photobiostimulation.

The terminal respitory chain oxidases in eukaryotic cells (cytochrome c oxides) and prokaryotic cells of *E. coli* (cytochrome bd complex) are believed to be photoreceptor molecules for red to NIR radiation. In the violet blue part of the spectrum flavoproteins (e.g. NADH-dehydrogenase in the beginning of the respiratory chain) are also among the photoacceptors and terminal oxidases.

There are many cellular photoreceptors and when illuminated there is a combined reaction. In many cases, it is not known which is the dominant receptor. These can be photochemical (typically at lower light doses) or photothermal (typically at higher doses) or a combination of both. Often times these result in a modulation of the redox state of the mitochondria (a shift in the direction of greater oxidation).

The mitochondria are cellular components that create the energy in the cell through respiration. The cellular metabolism can also be enhanced through photobiostimulation via activation of non-mitochondrial photoacceptors. This process is referred to as indirect activation or suppression.

Recent studies have shown that a number of nonphagocytic cell types, including fibroblasts, osteoblasts, endothelial cells, chondrocytes, kidney mesangial cells and others generate reactive oxygen species (mainly superoxide anion) in low concentration in response to optical stimuli.

Examples of Wavelengths and Power Levels

Table 2 below shows a number of different exemplary indications that can be treated with a product based on a replaceable diode laser. The table also shows exemplary power level and wavelengths for such treatment. As would be understood the listed indications are not meant to be limiting and such a device may also be applicable to other indications not listed.

TABLE 2 showing indications

| Indication | Typical Wavelength (nm) | Power level |
|---|---|---|
| Acne | 14xx | tens of watts |
| | 630 nm, 410 nm | <ten watts |
| | 400-1900 nm | |
| hair removal/inhibition | 750-900 | tens of watts->100 W |
| cellulite/fat/body sculpting | 750-1100, 930, 1210, nm | Up to 100 W |
| Veins, blood | 800-1000 | up to 100 Watts |
| Skin Rejuvenation | 14xx, 2700-2900 | tens of watts |
| | 620-1100 | <ten watts |
| | 400-1900 nm | <ten watts |
| fractional skin treatment | 750-3000 | multiple emitters each focused to a separate spot; lower power per spot |

TABLE 2-continued showing indications

| Indication | Typical Wavelength (nm) | Power level |
|---|---|---|
| rhytides/wrinkles | 14xx | tens of watts |
| pigments | 700-850 nm | tens of watts |
| photobiomodulation | 600-1000 nm | 0.01-20 W |

This table should not be considered limiting, just showing examples of best mode Use of Photonic Upconvertors Photonic upconverters describe a class of materials that when sufficiently illuminated will absorb multiple photons and emit at a shorter wavelengths. Since in most applications of this invention the laser is invisible, such a material can be used with the present invention to provide an indicator or to monitor the location of the laser on the skin. This would be useful in the case of a non-contact treatment. The upconverter could be mixed within a gel or light paste that could be applied topically to the treatment area of the skin. Since the materials have thresholds for illumination, such materials could also be useful to help define end of life of the disposable diode laser. If when illuminated the photonic upconverter emits visible light then the laser diode does not need to be replaced. If it does not emit, then it shows a lower than desirable power and means that the diode laser needs to be replaced. The measurement device could be the human eye or a spectrally sensitive photodiode attached to the handpiece.

Prescription Dosages

It may be the case that the regulations require a doctor to prescribe the light for the above treatments. If this is the case, the patient can be provided with a diode laser that has a known and finite lifetime and will be used for the specific treatment that is prescribed. The patient can keep the base unit and use it in the future with other diodes that he purchases OTC (over the counter) or by prescription.

Photopneumatic Therapy

Figure 10:
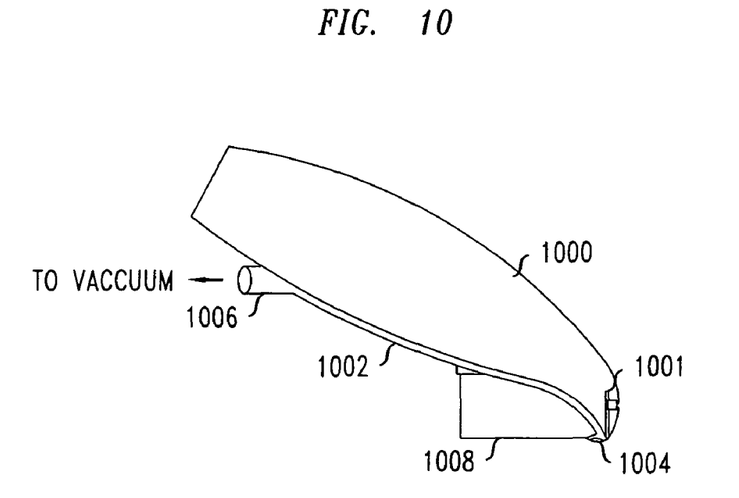
FIG. 10 is another exemplary embodiment of a laser treatment device in accordance with the present invention.

The application of pressure or using suction at the site of a photonic treatment has been shown to have favorable effects in aesthetic procedures. In hair removal, for example, applying suction compresses the skin and effectively makes it thinner. This results in a smaller amount of light to be scattered before it reaches the follicle. The thinner skin will bring the hair follicle closer to the surface. Inexpensive devices for applying suction or compression can be used in tandem with a disposable diode laser to enhance the efficacy of the procedure. Referring to FIG. 10, one exemplary embodiment of a laser treatment device 1000 having a replaceable laser diode module 1001 in accordance with the present invention is shown. The device 1000 includes a suction input 1004 that couples to tubing 1002 held in place on one side of the device 1000. The tubing has an outlet 1006 that couples to tubing for or directly to an external suction mechanism. As would be understood, the tubing could be internal to the handpiece of the device and the suction mechanism could be co-located or located within a base unit or charging station for the handpiece of the device. In certain embodiments, the suction mechanism may even be able to located within or adjacent to the handpiece. As described earlier, a holding element 1008 is also shown attached to the underside of the device for holding a cooling component such as ice in order to provide pre-treatment cooling to the skin prior to application of the laser. A thermoelectric cooler, as discussed could additionally be located in a similar location as the holding element.

In addition to those treatments already described, some of which may repeated herein, other treatments that are suitable for treatment by a device in accordance with the present invention may include hair removal treatment, hair reduction treatment, treatment for acne, treatment for body sculpting, treatment for fat reduction, treatment for collagen tightening, treatment for firming of the female breast, treatment for anti-aging, treatment for wrinkle reduction and/or fractional treatments, treatment for periorbital or perioral rhytides, treatment for lightening or removing pigments, medical treatment, treatment for photodynamic therapy, treatment for cold sores, treatment to relieve the symptoms of arthritis, musculoskeletal treatment, treatment for wound healing, treatment to reduce the appearance of scars or stretchmarks and treatment for photobiomodulation.

The foregoing description merely illustrates the principles of the invention. It will thus be appreciated that those skilled in the art will be able to devise various arrangements, which, although not explicitly described or shown herein, embody the principles of the invention, and are included within its spirit and scope. Furthermore, all examples and conditional language recited are principally intended expressly to be only for instructive purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. Many other modifications and applications of the principles of the invention will be apparent to those skilled in the art and are contemplated by the teachings herein. Accordingly, the scope of the invention is limited only by the claims.

What is claimed is:

1. A method for a laser treatment device utilizing GaAs laser diodes that are overdriven to shorten operational lifetime of said laser diodes comprising the steps of:
   providing a handpiece for provision of power to one or more laser light sources;
   providing a disposable laser diode module which couples and de-couples from said handpiece, said laser diode module having an electromechanical interface such that said laser diode module is replaceable by an ordinary user; and
   operating said GaAs laser diodes within said laser diode module at temperatures exceeding 50 degrees Celsius thereby shortening said operational lifetime of said laser diodes compared with operation at temperatures less than 50 degrees Celsius.

2. The method of claim 1, further including replacing the laser diode module subsequent to laser diodes within said module reaching a time or degradation threshold.

3. The method of claim 1, further including at least two single emitter laser diodes diced from at least one parallel configured laser bar and packaged in a series electrical configuration within said laser diode module.

4. The method of claim 1, further including operating the replaceable laser diode module at an output power adapted to a specific dermatological treatment.

5. The method of claim 1, wherein, the laser diode module is overdriven to operate at a power level to provide operation for approximately a five minute or less overall period, wherein said laser diode module is disposable.

6. The method of claim 1, wherein treatments suitable for treatment by said device are selected from the group consisting of: treatment for acne, treatment for body sculpting, treatment for fat reduction, treatment for collagen tightening, treatment for firming of the female breast, treatment for anti-aging, treatment for wrinkle reduction and/or fractional treatments, treatment for periorbital or perioral rhytides, treatment for lightening or removing pigments, medical treatment, treatment for photodynamic therapy, treatment for cold sores, treatment to relieve the symptoms of arthritis, musculoskeletal treatment, treatment for wound healing, treatment to reduce the appearance of scars or stretchmarks and treatment for photobiomodulation.

7. The method of claim 6 further including the step of applying a photonic upconverter topically to the skin of a user, wherein said photonic upconverter is used in connection with said device to provide uses selected from the group consisting of: monitoring the location of the invisible laser, as an indicator to monitor diode life, used in connection with a photodiode to monitor response to the laser diode and used within a skin applied substance as an indicator.

8. The method of claim 1, further including employing a suction mechanism for effectively compressing a skin area for laser treatment.

9. The method of claim 1, wherein said laser diode module has an emission wavelength in a range between 750-2000 nm.

10. The method of claim 1, wherein said laser diodes are secured in place by way of a non-permanent user alterable clamping technique, wherein a semiconductor piece is replaced by said user.

11. The method of claim 1, wherein a heatsink is included as part of said replaceable laser diode module.

12. The method of claim 11, wherein material for said heatsink is selected from the group consisting of copper, copper alloy, aluminum and aluminum alloy.

13. The method of claim 11, wherein the heatsink and a semiconductor diode are bonded with Indium based solder.

14. The method of claim 1, wherein said laser treatment device employs a cooling mechanism for cooling a skin area for laser treatment.

15. An apparatus for performing a laser light treatment comprising:
   a handpiece for provision of power to one or more laser diodes; and
   a replaceable and disposable laser diode module which couples and de-couples from said handpiece, said laser diode module having an electromechanical interface that enables said laser diode module to be replaceable by an ordinary user, wherein GaAs laser diodes within said laser diode module operate at temperatures exceeding 50 degrees Celsius.

16. The apparatus of claim 15, wherein said device is operable to give an indication to replace said laser diode module subsequent to laser diode module reaching a time or degradation threshold.

17. The apparatus of claim 15, further including at least two single emitter laser diodes diced from at least one parallel configured laser bar packaged in a series electrical configuration within said laser diode module.

18. The apparatus of claim 15, wherein, the laser diode module is overdriven to operate at a power level to provide operation for approximately a five minute or less overall period, said laser diode module being disposable.

19. The apparatus of claim 15, wherein said laser treatment device employs a suction mechanism for effectively compressing a skin area for laser treatment.

20. The apparatus of claim 15, wherein said laser diode module has an emission wavelength in a range between 750-2000 nm.

21. The apparatus of claim 15, wherein said laser diodes are secured in place by way of a non-permanent user alterable clamping technique.

22. The apparatus of claim 15, wherein a heatsink is included as part of said replaceable laser diode module.

23. The apparatus of claim 22, wherein material for said heatsink is selected from the group consisting of copper, copper alloy, aluminum and aluminum alloy.

24. The apparatus of claim 22, wherein the heatsink and a semiconductor diode are bonded with Indium based solder.

25. The apparatus of claim 15, wherein said laser treatment device employs a cooling mechanism for cooling a skin area for laser treatment.

26. The apparatus of claim 15, wherein a pulse duration output from said laser diode module is selected from the group consisting of: a duration between 1-100 ms, a duration between 1-1000 ms, a duration longer than 1000 ms and continuous operation.

27. The apparatus of claim 15, wherein the output power level of the laser diode module is between 1-500 Watts.

28. An apparatus for performing a laser light treatment, said apparatus utilizing GaAs laser diodes that are overdriven to thereby shorten operational lifetime of said laser diodes comprising:

a handpiece for provision of power to one or more laser diodes;

a replaceable laser diode module which couples and de-couples from said handpiece, said laser diode module having an electromechanical interface that enables said laser diode module to be replaceable by an ordinary user; and wherein said GaAs laser diodes within said laser diode module are overdriven to operate at temperatures exceeding 50 degrees Celsius thereby shortening said operational lifetime of said laser diodes compared with operation at temperatures less than 50 degrees Celsius.

\* \* \* \* \*